(12) United States Patent
Restrepo Restrepo et al.

(10) Patent No.: US 11,612,519 B2
(45) Date of Patent: Mar. 28, 2023

(54) REUSABLE TAMPON APPLICATOR (71) Applicant: PRODUCTOS FAMILIA S.A., Medellín (CO)

(72) Inventors: Catalina María Restrepo Restrepo, Medellín (CO); Dency Viviana Agudelo Velasquez, Medellín (CO); María Isabel Montaño Gómez, Rionegro (CO); Carolina Ospina Giraldo, Medellín (CO)

(73) Assignee: Productos Familia S.A., Medellín (CO)

( * ) Notice: Subject to any disclaimer, the term of this patent is extended or adjusted under 35 U.S.C. 154(b) by 0 days.

(21) Appl. No.: 17/039,987

(22) Filed: Sep. 30, 2020

(65) Prior Publication Data
US 2021/0378881 A1 Dec. 9, 2021

(30) Foreign Application Priority Data
Jun. 8, 2020 (CO) .......................... NC2020/0006998

(51) Int. Cl.
*A61F 13/26* (2006.01)
(52) U.S. Cl.
CPC .................................. *A61F 13/266* (2013.01)
(58) Field of Classification Search
CPC .............................. A61F 13/26; A61F 13/266
See application file for complete search history.

(56) References Cited

U.S. PATENT DOCUMENTS

| 2,351,836 | A | * | 6/1944 | Popper | ..................... | A61F 13/26 |
| | | | | | | 604/16 |
| 3,196,873 | A | * | 7/1965 | Bletzinger | ............. | A61F 13/26 |
| | | | | | | 604/15 |
| 4,286,594 | A | | 9/1981 | Cunningham | | |
| 9,427,361 | B2 | | 8/2016 | Buell et al. | | |
| 9,532,907 | B1 | | 1/2017 | Agrawal | | |
| 11,324,643 | B1 | * | 5/2022 | Samson | ................ | A61F 13/266 |
| 2002/0143287 | A1 | * | 10/2002 | Buzot | ................. | A61F 13/2085 |
| | | | | | | 604/14 |
| 2004/0078013 | A1 | * | 4/2004 | Zunker | ................... | A61F 2/005 |
| | | | | | | 604/355 |

(Continued)

FOREIGN PATENT DOCUMENTS

| CA | 1295093 C | 2/1992 |
| CL | 2009000684 | 1/2010 |

(Continued)

*Primary Examiner* — Susan S Su
(74) *Attorney, Agent, or Firm* — The Morales Law Firm; Joseph L. Morales, Esq.

(57) ABSTRACT

The present invention makes reference to a reusable tampon applicator, comprising a hollow cylindrical body with a first end having an opening and a second convex end, a gripping portion located on the first end, a slit formed by a first slit section extending from the second convex end along the surface of the cylindrical body, and a second slit section extending symmetrically towards the first slit section from the second end. The reusable tampon applicator also includes a plunger which is inserted into the hollow cylindrical body through the opening of the first end, where the first slit section has a length greater than the length of the second slit section, and furthermore, the slit section located at the second convex end describes an oval, wherein a tampon is inserted within the cylindrical body.

21 Claims, 4 Drawing Sheets

(56) References Cited

U.S. PATENT DOCUMENTS

| | | | | |
|---|---|---|---|---|
| 2012/0204410 A1* | 8/2012 | Mastalish | ............... | A61F 13/26 29/505 |
| 2012/0226216 A1* | 9/2012 | Conroy | ................ | A61F 13/266 604/11 |
| 2014/0155810 A1* | 6/2014 | Buell | .................... | A61F 13/263 604/16 |
| 2017/0020744 A1* | 1/2017 | Agrawal | ............. | A61F 13/2097 |
| 2018/0243125 A1* | 8/2018 | Callaghan | ............... | A61F 13/28 |

FOREIGN PATENT DOCUMENTS

| | | |
|---|---|---|
| CL | 2015003762 | 8/2016 |
| DE | 3910458 C1 | 9/1990 |
| EP | 2821042 A1 | 1/2015 |
| ES | 443622 A1 | 5/1977 |
| WO | 2009119597 A1 | 10/2009 |
| WO | 2012107880 A2 | 8/2012 |

* cited by examiner

REUSABLE TAMPON APPLICATOR

FIELD OF THE INVENTION

The present invention is related to the field of feminine care products. Specifically, the present invention relates to tampon applicators.

DESCRIPTION OF THE STATE OF THE ART

Currently, and taking into account the high amount of material used in tampons and in the disposable applicators thereof, there has been a need to develop tampon applicators that can be reusable. Accordingly, prior art discloses reusable tampon applicators as in U.S. Pat. No. 9,532,907B1, U.S. Pat. No. 9,427,361B2.

In particular, U.S. Pat. No. 9,532,907B1 discloses a reusable tampon applicator comprising a cylindrical body, a pusher for driving a tampon through the cylindrical body during insertion of the tampon, and a cover that allows the cylindrical body to be housed. Said cylindrical body comprises an opening at a distal end of the cylindrical body for inserting the tampon and a convex apex at a proximal end. Additionally, said cylindrical body comprises an opening for the tampon to pass through during insertion of the tampon. A slit extends from the proximal end to the distal end of the cylindrical body to form a complete slit in a first lateral side of the cylindrical body. Said slit further extends from the proximal end towards the distal end to form a partial slit on a second lateral side. Additionally, U.S. Pat. No. 9,532,907B1 notes that the partial slit and the full slit can have the same uniform width.

For its part, U.S. Pat. No. 9,427,361B2 discloses a tampon applicator and a cap having a closed end and an open end. The tampon applicator has a cylinder to house an absorbent element and a plunger to dispose the absorbent element. The plunger has an end portion that is a cap that connects to the rest of the plunger and engages the cap at the open end, to provide a seal with the cap that completely encloses the tampon applicator.

U.S. Pat. No. 9,532,907B1 also describes an assembly having a tampon applicator, a cap having a closed end and an open end, and a cap's cap to cover the open end of the cap. U.S. Pat. No. 9,532,907B1 also indicates that in other embodiments, there may be a plurality of grooves along at least a portion of the length of the cylinder.

Therefore, although tampon applicators are described in both patent documents, in both cases the plunger must be removed from the first slit in order to insert an absorbent element, such as a tampon. Additionally, said applicators are not sufficiently ergonomic, thus allowing some of the component parts to fall from the hands of a user, and furthermore, the slits through which said tampon is withdrawn can cause it to wear out or detach unwanted filaments.

BRIEF DESCRIPTION OF THE INVENTION

The present invention relates to a reusable tampon applicator, comprising a hollow cylindrical body having a first end with an opening and a second convex end, a gripping portion located at the first end, a slit formed by a first slit section extending from the second convex end along the surface of the cylindrical body, and a second slit section extending symmetrically to the first slit section from the second end.

The reusable tampon applicator also includes a plunger which is inserted into the hollow cylindrical body through the opening of the first end, wherein the first slit section has a length greater than the length of the second slit section, and furthermore, the section of the slit located at the second convex end describes an oval. Said tampon applicator allows a user to insert the tampon into the hollow cylindrical body through the oval that is described by the section of the slit located at the second convex end, thus avoiding that some of the tampon applicator parts fall from the user's hands. Additionally, the cylindrical body has an external surface wherein a cover may be located in order to protect the cylindrical body from damage.

DETAILED DESCRIPTION

The present invention relates to a reusable tampon applicator, comprising a cylindrical body that is hollow with a first end having an opening and a second convex end, a gripping portion located at the first end, a slit formed by a first slit section extending from the second convex end along the surface of the cylindrical body, and a second slit section extending symmetrically towards the first slit section from the second end.

The reusable tampon applicator also includes a plunger which is inserted into the cylindrical body through the opening of the first end, wherein the first slit section has a length greater than the length of the second slit section, and furthermore, the slit section located at the second convex end describes an oval.

Figure 1:
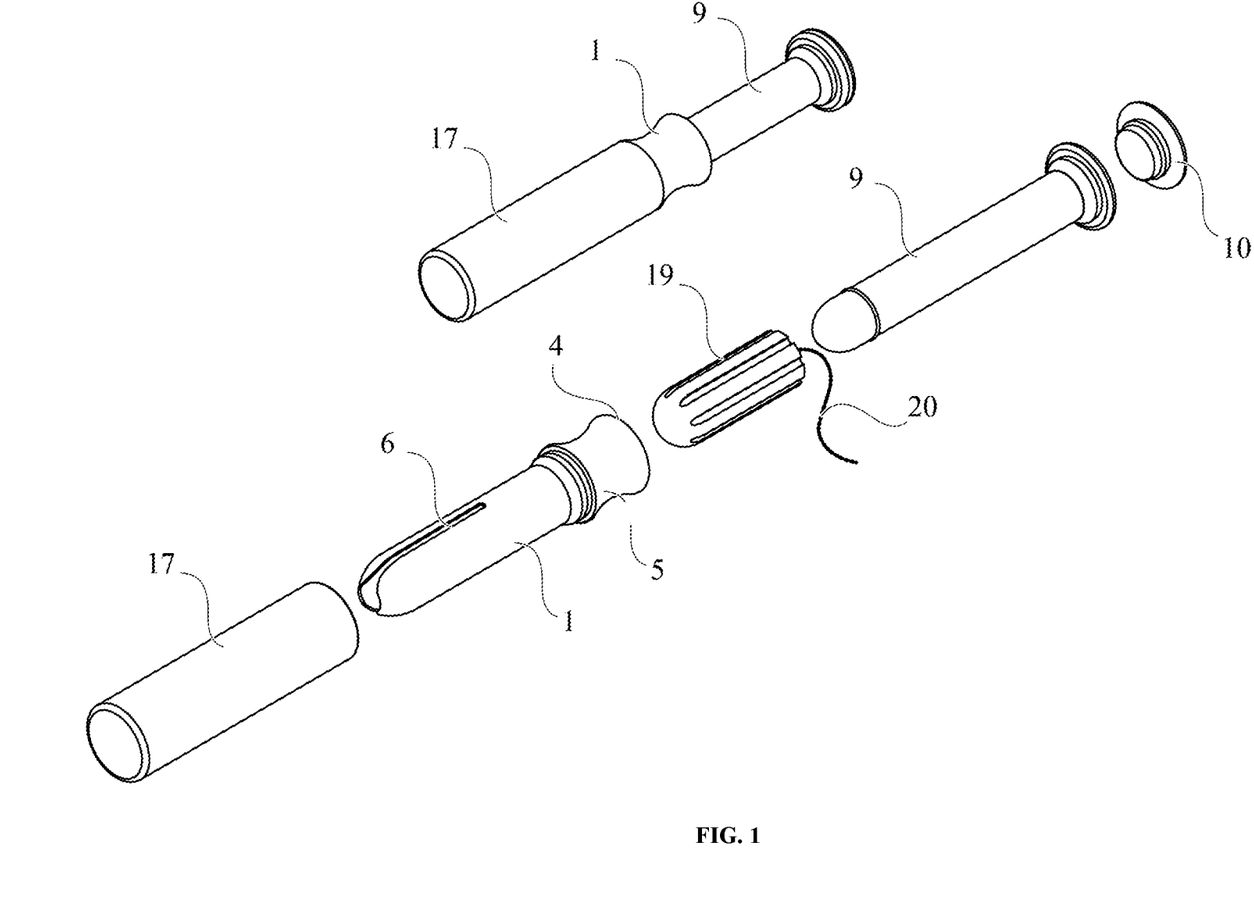
FIG. 1 illustrates two views of a reusable tampon applicator, wherein one of the views illustrates a cover, a cylindrical body, a tampon, a plunger and a cap in an exploded view, and the other view shows the aforementioned elements assembled together.
Figure 2:
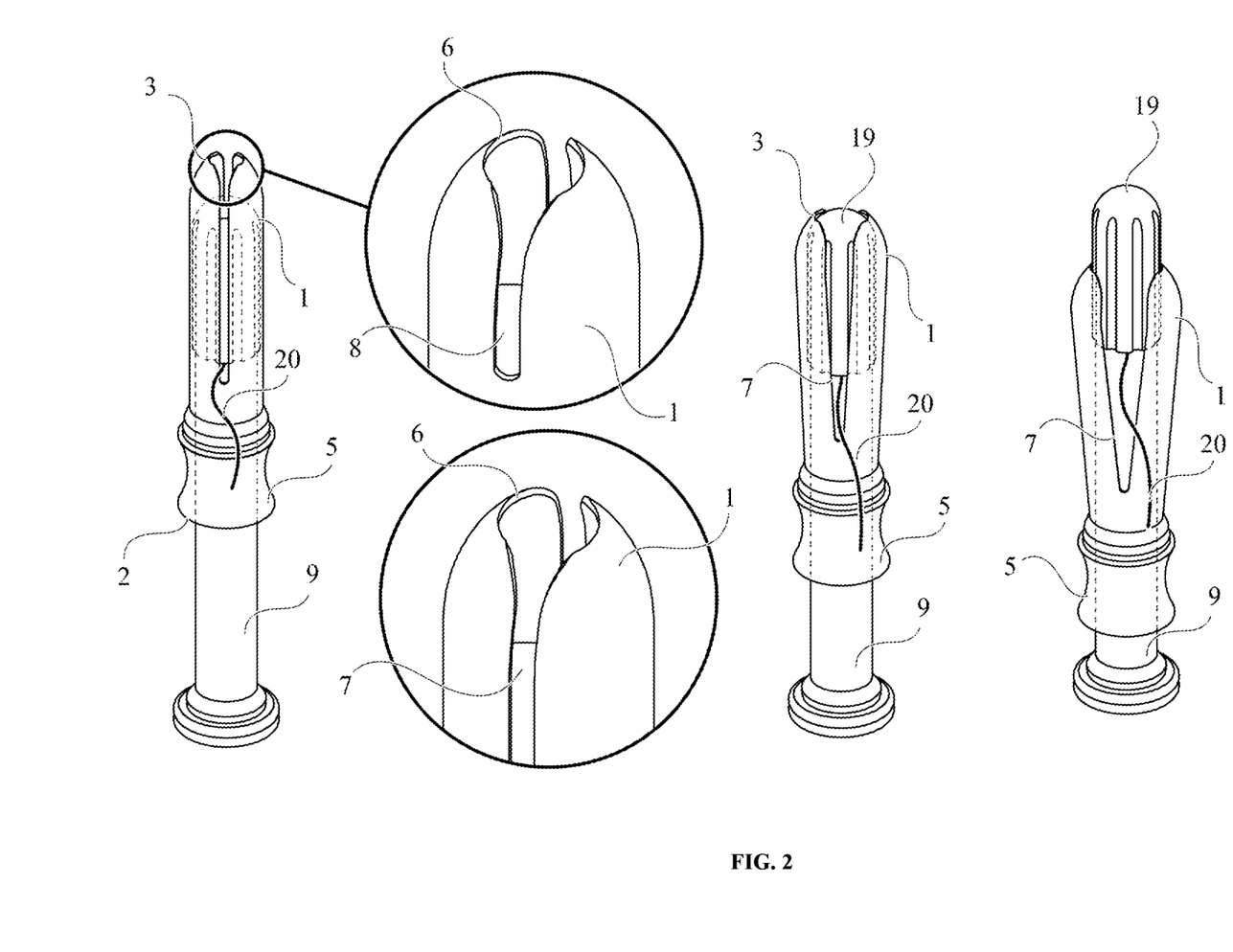
FIG. 2 illustrates three views of the tampon applicator of FIG. 1 wherein a tampon is arranged within the cylindrical body, and in each of the three views the tampon is illustrated moving within the cylindrical body.

Referring to FIG. 1 and FIG. 2, the reusable tampon applicator comprises a cylindrical body (1) with a first end (2) having an opening (4) and a second convex end (3), a gripping portion (5) located on the cylindrical body (1) and contiguous to the first end (2). Said reusable applicator also includes a slit (6) formed by a first slit section (7) that extends from the second convex end (3) along the surface of the cylindrical body (1). Additionally, a second slit section (8) extends symmetrically towards the first slit section (7) from the second end (3) along the surface of the cylindrical body (1). For the understanding of the present invention, it will be understood that the length of the cylindrical body (1) corresponds to the distance between the first end (2) and the second end (3), while the width corresponds to the cross length of the cylindrical body (1).

Additionally, and referring to FIG. 1, a plunger (9) is inserted into the cylindrical body (1) through the opening (4) of the cylindrical body (1). Furthermore, the slit section (6) located at the second convex end (3) describes an oval, i.e., in said section, the slit has an oval-shape perforation.

Referring to FIG. 2, when a tampon (19) is located inside the cylindrical body (1), a user holds the cylindrical body (1)

by the gripping portion (5) of the cylindrical body (1). Subsequently, the user drives the plunger (9) inserted in the cylindrical body (1) through the opening (4), thus driving the tampon (19) towards the slit section (6) located at the second convex end that describes an oval, expelling the tampon (19) from the cylindrical body (1) there through.

As mentioned above and referring to FIG. 1, and FIG. 2, the cylindrical body (1) is a hollow element, preferably cylindrical, with a first end (2) having an opening (4), and a second end (3) with a convex end. Said cylindrical body (1) has a slit (6) formed by a first slit section (7) and a second slit section (8). The first slit section (7) extends from the second convex end (3) along the surface of said cylindrical body (1). The second slit section (8) extends symmetrically towards the first slit section from the second end. Wherein preferably, the first slit section (7) has a length greater than the length of the second slit section (8).

On the other hand, the slit (6) located at the second convex end (3) describes an oval, i.e., at said second end (3), the slit (6) is an oval-shaped perforation, which allows inserting a tampon (19) through said slit section (6).

This allows a user not to separate the plunger (9) from the cylindrical body (1) in order to insert the tampon (19) into the slit (6) of the cylindrical body (1), i.e., it is not necessary to insert the tampon (19) through the opening (4) where the plunger (9) is inserted. This improves ergonomics and makes it easier for a user to use the tampon applicator without any of the three elements, the cylindrical body (1), the plunger (9) or the tampon (19), falling out of the user's hands. Additionally, given the slit (6) has an oval shape at the second end (3) of the cylindrical body (1), it allows that, when the plunger (9) pushes a tampon (19) through said slit (6), said tampon (19) does not suffer damage or detach unwanted fibers because the oval shape avoids sharp corners (also called sharp edges), thus aiding the tampon (19) in smoothly sliding within the cylindrical body (1).

Additionally, and referring to FIG. 2, the first slit section (7) preferably has a length greater than the length of the second slit section (8). The foregoing allows said slit (6) to open, i.e., to increase the width of the slit (6) to allow the exit or entry of a tampon (19). On the other hand, when the first slit section (7) has a greater length than the second slit section (8) and the tampon (19) is being ejected or entered into the cylindrical body (1), the first slit section (7) opens more in comparison than the second slit section (8). This prevents the tampon (19) from falling easily through the second slit section (8) of the cylindrical body (1).

Furthermore, and referring to FIG. 2, given the first slit section (7) has a greater length compared to the second slit section (8), it allows that when a tampon (19) is inserted through the second end (3) of the cylindrical body (1), the string (20) of the tampon (19) preferably exits through the first slit section (7). This prevents said string (20) from getting stuck between the plunger (9) and the internal surface of the cylindrical body (1), and thus preventing said string (20) from being cut.

On the other hand, the gripping portion (5) of the cylindrical body (1) corresponds to an area that is held by a user when using the tampon applicator. When a user is about to utilize the tampon applicator, she holds the cylindrical body (1) by the grip portion (5) to insert the tampon (19) through the slit (6). When the user requires ejecting the tampon (19) from the cylindrical body (1), the user again grasps the gripping portion (5) and pushes the plunger (9) into the cylindrical body (1) in order to expel the tampon (19).

In one embodiment of the invention, the gripping portion (5) has a shape selected from the group consisting of cones, truncated cones, discs, prisms, cubes, spheres, cuboid, parallelepipeds, cylinders, hyperbole, hyperboloid, hoppers, and combinations thereof. Given the grip portion (5) has one of the previously described shapes, it allows a user to touch feel a different surface than the rest of the cylindrical body (1), which allows it to have more friction, and know precisely that the cylindrical body (1) must be held there. Additionally, some of said shapes can provide greater contact area for a user to hold said gripping portion (5). Preferably, the gripping portion (5) has a greater width compared to the rest of the cylindrical body (1), thus allowing the user to identify the surface by which she must grip the cylindrical body (1).

Additionally, and referring to FIGS. 1, 2, 3 and 4, the grip portion (5) preferably has a shape related to a hyperboloid, allowing a user to grip the cylindrical body (1). It also makes it possible to increase the contact area between the fingers of a user and the cylindrical body (1), and further prevents the fingers of a user from moving or slipping along the cylindrical body (1).

On the other hand, the materials of the cylindrical body (1) are medical or sanitary grade materials allowing them not to generate irritations or damage to the health of the person who is going to use the tampon applicator. The material is selected from the group consisting of low-density polyethylene (LDPE), acrylonitrile butadiene styrene (ABS), polypropylene (PP), medical grade silicone, polyethylene (PE), polypropylene (PP), and other polymers such as polycarbonate (PC), polytetrafluoroethylene (PTFE), polyurethane (PUR), polymethylmethacrylate (PMMA), lactic polyacid (PLA), polyethylene glycol terephthalate (PETG), nylon, high impact polystyrene (HIPS), equivalent materials known to a normally skilled person, or combinations thereof.

The material of the cylindrical body (1) is preferably a medical grade low-density polyethylene (LDPE), given this is a material especially used for the manufacture of sanitary ware.

Moreover, the plunger (9) is an element that is inserted into the cylindrical body (1), and whose external shape preferably coincides with the internal shape of the cylindrical body (1), i.e., when the internal surface of the cylindrical body (1) is a cylinder, the outer surface of the plunger (9) is also a cylinder.

Said plunger (9) has two ends, a first end and a second end, and it can be solid, or it can be hollow. When the plunger (9) is hollow, the amount of material necessary for the manufacture of the plunger (9) is reduced, and furthermore its weight is reduced. In reference to FIG. 3, when said plunger (9) is hollow, the first end of the plunger (9) drives the tampon (19) into the cylindrical body (1), and the second end, corresponding to the open end, is sealed by a cap (10).

For the understanding of the present invention, protrusion will be understood as a prominence or elevation of something on a surface. For example, when the plunger (9) has a protrusion on its external surface, said protrusion is a raised surface compared to the rest of the external surface of the plunger (9). Accordingly, for the understanding of the present invention, a groove will be understood as a generally narrow and long channel, where a protuberance is inserted.

In an embodiment of the invention, the cylindrical body (1) has an internal surface, where said internal surface has a first groove (11), and the plunger (9) has an external surface that has a first protrusion (13). This allows for when the plunger (9) is inside the cylindrical body (1), the first protrusion (13) of the plunger (9) is inserted into the first groove (11) of the cylindrical body (1).

Figure 4:
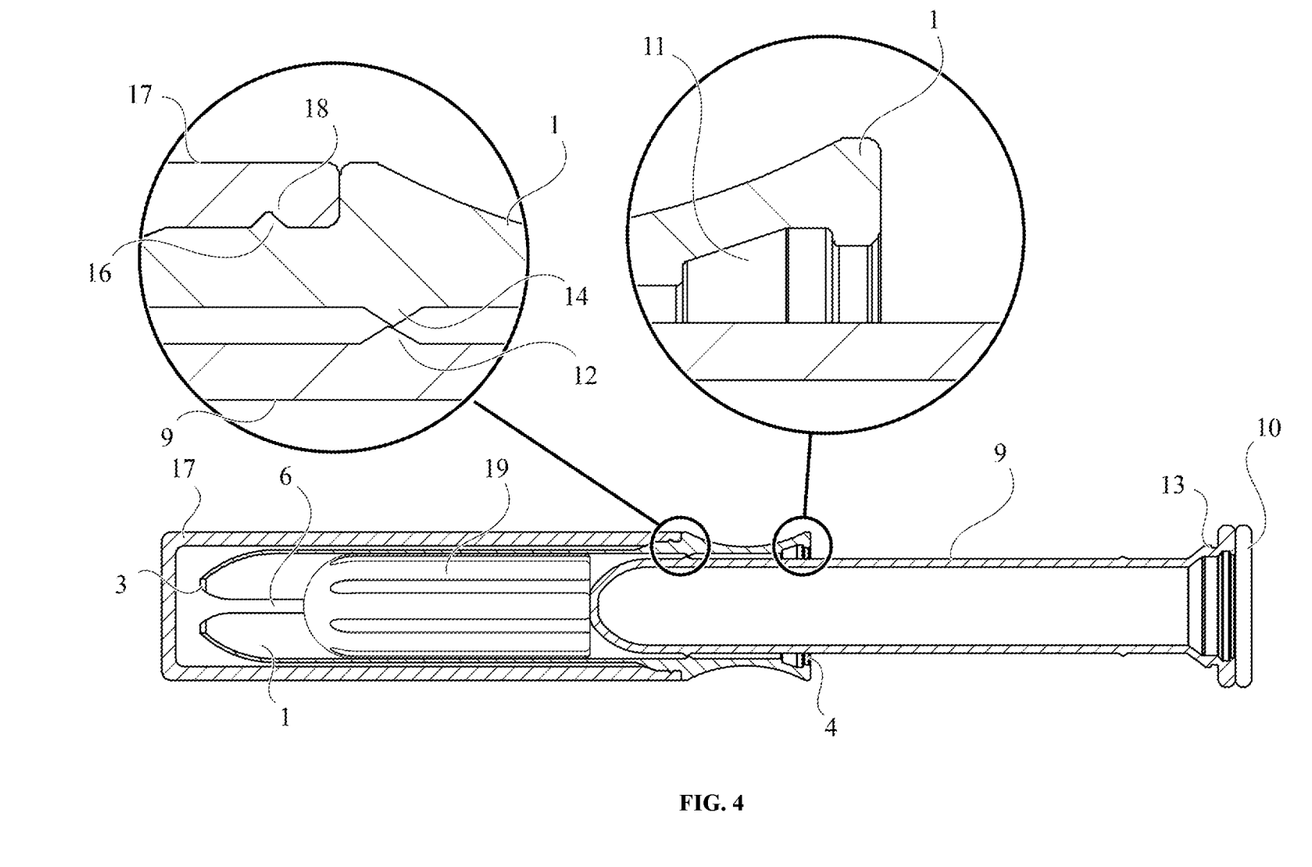
FIG. 4 illustrates the tampon applicator of FIG. 1 in a side sectional view, wherein two details of the connection between the cylindrical body and the cover are shown.

Referring to FIG. 4, the cylindrical body (1) has a first groove (11) close to the first end (2), and the plunger (9) has a first protrusion (13) at the second end, i.e., the second end is the one gripped and driven by a user to slide a tampon (19) within the cylindrical body (1). In said embodiment, when the plunger (9) is completely inside the cylindrical body (1), the first protrusion (13) engages in the first groove (11) thus allowing the plunger (9) not to separate from the cylindrical body (1) when the tampon applicator is not in use unless an external force is exerted on said elements.

On the other hand, the plunger (9) may have a second protrusion (12) on its external surface and the cylindrical body (1) may have a second groove on its internal surface, allowing the second protrusion (12) to be inserted into the second groove of the plunger (9) when the plunger (9) is inside the cylindrical body (1). Preferably, the second groove is located in an intermediate zone on the inner surface of the cylindrical body (1). This allows for the second slot to engage with the second protrusion (12) when a user inserts a tampon (19) into the cylindrical body (1) through the slit (6), thus allowing the plunger (9) not to separate from the cylindrical body (1) during the tampon application.

In one embodiment of the invention, and referring to FIG. 4, the cylindrical body (1) has a third protrusion (14) on its internal surface and the plunger (9) may in turn have a second protrusion (12). This allows for the second protrusion (12) to prevent the plunger (9) from moving completely within the cylindrical body (1) when a user inserts a tampon (19) into the cylindrical body (1) through the slit (6). This is because the third protrusion (14) comes into contact with the second protrusion (12), thus allowing the plunger (9) not to separate from the cylindrical body (1) during the tampon application.

On the other hand and in reference to FIG. 4, when the plunger (9) has a first protrusion (13) and a second protrusion (12), both located on the outer surface of the plunger (9), they can brace said surface as a ring, and accordingly, the first groove (11) and the second groove of the inner surface of the cylindrical body (1) may also brace said inner surface. This allows the protrusions to join the grooves regardless of whether the plunger (9) rotates within the cylindrical body (1). Similarly, when the cylindrical body (1) has a third protrusion (14), said protrusion may brace said surface like a ring.

Additionally, each of said protrusions, both those of the plunger (9) or those of the cylindrical body (1), may be part of the same body, or they may be of a different material and be attached to the plunger (9) or to the cylindrical body (1) respectively. For example, each of said protrusions can be an O-ring arranged around the plunger (9) or on the internal surface of the cylindrical body (1).

For the understanding of the present invention, a cover (17) will be understood as any cover, element, sheet or plate which is arranged on the external surface of the cylindrical body (1).

Figure 3:
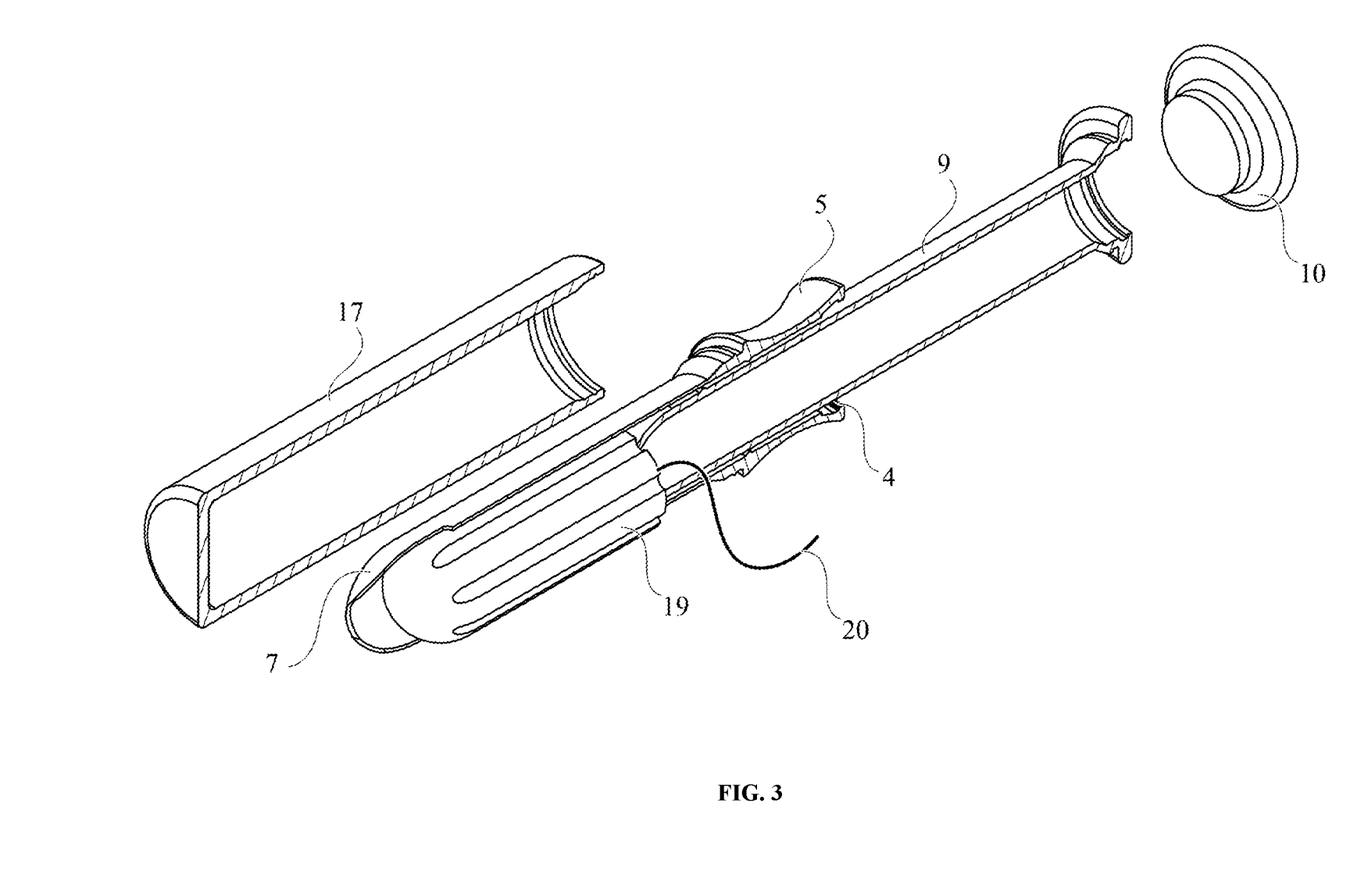
FIG. 3 illustrates the tampon applicator of FIG. 1 in a side sectional view.

Referring to FIG. 1, FIG. 3 and FIG. 4, the cylindrical body (1) has an external surface on which a cover (17) can be arranged, which allows protecting the cylindrical body (1) from damage, scratches or contamination. The cover (17) has an internal surface that can totally or partially touch the external surface of the cylindrical body (1).

Preferably, the cover (17) covers the entire outer surface of the cylindrical body (1) except the outer surface of the gripping portion (5), thus allowing a user to grip the cylindrical body (1) by its gripping portion (5), subsequently hold the cover (17), and remove the cover (17) from the cylindrical body (1).

In one embodiment of the invention, and referring to FIG. 4, the cylindrical body (1) has on its external surface a fourth protrusion (16), and the cover (17) has an internal surface which has a third groove (18). This allows for the fourth protrusion (16) of the cylindrical body (1) to be inserted into the third slot (18) of the cover (17) when the cover (17) is arranged on the external surface of the cylindrical body (1), thus allowing the cylindrical body (1) and the cover (17) to remain together until an external force is exerted on the cylindrical body (1) and the cover (17).

The fourth protrusion (16) can surround the outer surface of the cylindrical body (1) like a ring, and can be part of the same body, or it can be of a different material. For example, said fourth protrusion (16) can be an O-ring surrounding the cylindrical body (1).

The material of the cover (17) can be a flexible material, or a rigid material. The cover (17) can be made of any of the following materials: metal, plastic, low density polyethylene (LDPE), acrylonitrile butadiene styrene (ABS), polypropylene (PP) and medical grade silicone. Polyethylene (PE), polypropylene (PP), and other polymers such as polycarbonate (PC), polytetrafluoroethylene (PTFE), polyurethane (PUR), polymethylmethacrylate (PMMA), polyacid lactic acid (PLA), polyethylene terephthalate glycol (PETG), Nylon, high impact polystyrene (HIPS), equivalent materials known to a normally skilled person, or combinations thereof.

EXAMPLE 1

Referring to FIG. 1 and FIG. 2, a reusable tampon applicator was constructed comprising a cylindrical body (1) with a first end (2) having an opening (4) and a second convex end (3), a gripping portion (5) located on the cylindrical body (1) and adjacent to the first end (2), a slit (6) formed by a first slit section (7) extending from the second convex end (3) along the surface of the cylindrical body (1), and a second slit section (8) extending symmetrically towards the first slit section (7) from the second end (3) along the surface of the cylindrical body (1).

Said first slit section (7) has a greater length compared to the second slit section (8). Additionally, and referring to FIG. 4, the cylindrical body (1) has a first slot (11) located at the end adjacent to the first end (2), while the plunger (9) has a first protrusion (13).

EXAMPLE 2

Referring to FIGS. 1, 2, 3 and 4, a reusable tampon applicator was developed like the one in Example 1 wherein the plunger (9) with a first and second end, comprised a second groove (12) at a point between the first and second ends. Additionally, the cylindrical body (1) had a second groove on its internal surface, which made it possible to couple the plunger (9) with the cylindrical body (1).

EXAMPLE 3

Referring to FIGS. 1, 2, 3 and 4, a reusable tampon applicator was developed as in Example 1 or Example 2 wherein the grip portion (5) has a hyperboloid shape. In said example 3, a cover (17) was arranged on the cylindrical body (1) until reaching the gripping portion (5), i.e., said cover (17) covered the external surface of the cylindrical body (1) except for the external surface of the gripping portion (5).

EXAMPLE 4

Referring to FIGS. 1, 2, 3 and 4, a reusable tampon applicator was developed as in Example 1, Example 2, and Example 3, where the cylindrical body (1) was made of medical grade low-density polyethylene (LDPE), having the following properties:
Density: 0.9 g/cm$^3$-0.93 g/cm$^3$;
melting point: 105° C.-115° C.;
maximum tensile stress (MPa): 8-23;
Charpy impact resistance (kJ/m$^2$): 61; and
additionally, it was medical grade and additive free.

Moreover, the material of the plunger (9) and of the cover (17) was polypropylene and had the following properties:
Density: 0.9 g/cm$^3$-0.92 g/cm$^3$;
melting point: 130° C.-170° C.;
maximum tensile stress (MPa): 21-37;
Charpy impact resistance (kJ/m$^2$): 4-40; and
Shore D hardness: 67-74.

It should be understood that the present invention is not limited to the embodiments described and illustrated herein, since as will be evident to a normally skilled person, there are variations and possible modifications that do not depart from the spirit of the invention, which are only defined by the following claims.

The invention claimed is:

1. A reusable tampon applicator, comprising:
an elongate hollow cylindrical body having a first end including a plunger opening, and a convex second end longitudinally opposite said first end, said convex second end having a tampon opening configured to receive a tampon therethrough and into an interior thereof, said tampon opening including a pair of diametrically opposed slits extending from a central portion of said tampon opening at said convex second end and toward said plunger opening;
a plunger coupled to said hollow cylindrical body through said plunger opening and slidably movable within said interior of said hollow cylindrical body; and
a plurality of interlocking elements preventing separation of said plunger from said hollow cylindrical body.

2. The reusable tampon applicator of claim 1, wherein said plurality of interlocking elements includes one or more protrusions on a surface of said plunger engageable with a cooperating one or more grooves in said interior of said hollow cylindrical body.

3. The reusable tampon applicator of claim 1, wherein said pair of diametrically opposed slits includes a first slit and a second slit shorter in length than said first slit.

4. The reusable tampon applicator of claim 3, wherein both of said first and second slits are spaced from said plunger opening.

5. The reusable tampon applicator of claim 1, wherein said central portion of said tampon opening at said convex second end is generally oval in shape.

6. The reusable tampon applicator of claim 1, wherein said tampon opening is free of sharp edges.

7. The reusable tampon applicator of claim 1, wherein said plunger is hollow.

8. The reusable tampon applicator of claim 1, wherein said hollow cylindrical body is made of a medical grade material.

9. The reusable tampon applicator of claim 8, wherein said hollow cylindrical body is made of medical grade low-density polyethylene (LDPE).

10. The reusable tampon applicator of claim 1, further comprising a gripping portion at said first end of said hollow cylindrical body, wherein
said gripping portion has a greater diameter than a remainder of said hollow cylindrical body,
said gripping portion is integrally formed with said hollow cylindrical body, and
said gripping portion has a concave shaped outer surface.

11. A reusable tampon applicator, comprising:
an elongate hollow cylindrical body having a first end including a plunger opening, and a convex second end longitudinally opposite said first end, said convex second end having a tampon opening configured to receive a tampon therethrough and into an interior thereof, said tampon opening including a pair of diametrically opposed first and second slits extending from a central portion of said tampon opening at said convex second end and toward said plunger opening, said first and second slits being of different lengths and both being spaced from said plunger opening;
a plunger coupled to said hollow cylindrical body through said plunger opening and slidably movable within said interior of said hollow cylindrical body; and
a plurality of interlocking elements preventing separation of said plunger from said hollow cylindrical body.

12. The reusable tampon applicator of claim 11, further comprising a gripping portion at said first end of said hollow cylindrical body and having a greater diameter than a rest of said hollow cylindrical body, said hollow cylindrical body being made of medical grade low-density polyethylene (LDPE).

13. The reusable tampon applicator of claim 11, further comprising a gripping portion at said first end of said hollow cylindrical body, wherein
said gripping portion has a greater diameter than a remainder of said hollow cylindrical body,
said gripping portion is integrally formed with said hollow cylindrical body, and
said gripping portion has a hyperboloid shaped outer surface.

14. A reusable tampon applicator comprising:
an elongate hollow cylindrical body having a first end including a plunger opening, and a convex second end longitudinally opposite said first end, said tampon opening including a pair of diametrically opposed slits extending from a central portion of said tampon opening at said convex second end and toward said plunger opening;
a plunger coupled to said hollow cylindrical body through said plunger opening and slidably movable within said interior of said hollow cylindrical body;
a plurality of interlocking elements preventing separation of said plunger from said hollow cylindrical body; and
a gripping portion at said first end of said hollow cylindrical body,
wherein
said gripping portion has a greater diameter than a remainder of said hollow cylindrical body,
said gripping portion is integrally formed with said hollow cylindrical body, and
said gripping portion has a concave shaped outer surface.

15. A method of loading a tampon into a reusable tampon applicator, the method comprising:
obtaining an elongate tampon;

obtaining an elongate reusable tampon applicator including a hollow cylindrical body having an interior and a plunger, the reusable tampon applicator having a plunger opening at a first longitudinal end thereof and a tampon opening at a second longitudinal end thereof, the plunger opening being configured to receive the plunger therethrough into the interior of the hollow cylindrical body; and inserting the tampon through the tampon opening and into the interior of the hollow cylindrical body.

16. The method of claim 15, further comprising inserting the plunger into the hollow cylindrical body through the plunger opening.

17. The method of claim 16, wherein inserting the tampon through the tampon opening and into the interior of the hollow cylindrical body is performed subsequent to inserting the plunger into the hollow cylindrical body through the plunger opening.

18. The method of claim 15, wherein the hollow cylindrical body includes an integrally formed gripping portion larger in diameter than a remainder of the hollow cylindrical body, the method further comprising supporting the tampon applicator from the gripping portion while inserting the tampon through the tampon opening and into the interior of the hollow cylindrical body.

19. The method of claim 18, further comprising supporting the tampon applicator from the gripping portion while inserting the plunger through the plunger opening and into the interior of the hollow cylindrical body.

20. The method of claim 18, wherein the gripping portion has a concave outer surface.

21. The method of claim 15, wherein the tampon includes a string, the method further comprising extending the string through a slitted section of the tampon opening toward an exterior of the hollow cylindrical body during insertion of the tampon into the interior of the hollow cylindrical body.

* * * * *